United States Patent
Krumme

(10) Patent No.: US 7,634,046 B2
(45) Date of Patent: Dec. 15, 2009

(54) COMPUTER TOMOGRAPH WITH NON-CONTACTING ENERGY TRANSMISSION

(75) Inventor: Nils Krumme, Feldafing (DE)

(73) Assignee: Schleifring und Apparatebau GmbH, Fuerstenfeidbruck (DE)

(*) Notice: Subject to any disclaimer, the term of this patent is extended or adjusted under 35 U.S.C. 154(b) by 37 days.

(21) Appl. No.: 10/596,027

(22) PCT Filed: Nov. 27, 2003

(86) PCT No.: PCT/EP03/13354
§ 371 (c)(1),
(2), (4) Date: Nov. 21, 2006

(87) PCT Pub. No.: WO2005/064625
PCT Pub. Date: Jul. 14, 2005

(65) Prior Publication Data
US 2007/0195924 A1 Aug. 23, 2007

(51) Int. Cl.
*H05G 1/02* (2006.01)
*H05G 1/10* (2006.01)

(52) U.S. Cl. .............. 378/19; 378/4; 378/101; 378/197

(58) Field of Classification Search .......... 378/4, 378/19, 101, 196, 197, 204, 210
See application file for complete search history.

(56) References Cited

U.S. PATENT DOCUMENTS

| | | | |
|---|---|---|---|
| 4,912,735 A | 3/1990 | Beer | |
| 5,023,768 A * | 6/1991 | Collier | 363/68 |
| 5,608,771 A | 3/1997 | Steigerwald et al. | |
| 6,433,631 B2 | 8/2002 | Pearson, Jr. et al. | |
| 6,563,717 B2 * | 5/2003 | Lunding et al. | 363/15 |
| 6,674,836 B2 * | 1/2004 | Harada et al. | 378/107 |
| 7,054,411 B2 * | 5/2006 | Katcha et al. | 378/101 |
| 7,197,113 B1 * | 3/2007 | Katcha et al. | 378/101 |
| 2001/0008552 A1 | 7/2001 | Harada et al. | |

FOREIGN PATENT DOCUMENTS

| | | |
|---|---|---|
| DE | 3923525 | 3/1990 |
| DE | 4412958 | 10/1995 |
| DE | 19649682 | 6/1998 |
| DE | 10037294 | 1/2002 |
| JP | 8-336521 | 12/1996 |

OTHER PUBLICATIONS

International Search Report, PCT/EP03/13354, mailed Jun. 7, 2004.

* cited by examiner

*Primary Examiner*—Allen C. Ho
*Assistant Examiner*—Thomas R Artman
(74) *Attorney, Agent, or Firm*—Kevin L. Daffer; Daffer McDaniel, LLP

(57) ABSTRACT

A computer tomograph system comprises a rotating part for accommodating at least one X-ray tube and a detector arrangement, and a stationary part rotatably supporting the rotating part, and comprising a DC-to-AC converters for generating an alternating current for supplying current to a conductor arrangement. To supply energy to the rotating part, the rotating part comprises at least one inductive coupler for engaging, exclusively in dependence upon position, with a section of the entire length of the conductor arrangement, and for coupling electrical energy out of the conductor arrangement. Alternatively, the conductor arrangement may be disposed on the rotating part, and the inductive coupler may be disposed on the stationary part.

26 Claims, 7 Drawing Sheets

COMPUTER TOMOGRAPH WITH NON-CONTACTING ENERGY TRANSMISSION

BACKGROUND OF THE INVENTION

1. Technical Field

The invention relates to a computer tomograph with non-contacting transmission of energy. In this, the transmission of the energy needed by an X-ray tube is effected without contact between a stationary current supply and an X-ray tube disposed to be rotatable. Simultaneously, current may be supplied to other consumers such as detectors or data processing systems on the rotating part.

2. Description of the Prior Art

With conventional computer tomographs a transmission of electrical energy between a stationary current supply and a rotating part is effected by means of mechanical slip-ring systems. In this, a brush, preferably of a carbon material, slides along a slide track, for example of brass. Disadvantages of this arrangement are a low lifetime, regular servicing intervals in which the brushes must be changed, and contamination by abrasion of the carbons.

An improvement is disclosed, for example, in U.S. Pat. No. 4,912,735. In this, the computer tomograph system is configured to be a rotating data transmission device. A primary winding, fed by a primarily disposed alternating current source, is located on a stationary side. A secondary winding is mounted opposite to this on a rotating side. For better coupling between the primary winding and the secondary winding, these are surrounded by rotationally symmetrical cores of magnetically soft materials. However, this device is not suitable for transmitting high power in a range of 100 kilowatts, as would be necessary to energize modern X-ray tubes. This is because the transmission device has a high stray inductance owing to unavoidable air gaps between the stationary and the rotating side. Electrically this acts like a series inductance and thus represents a high series impedance for the current to be transmitted, which limits the transmittable power.

Another improvement is disclosed in U.S. Pat. No. 5,608,771. Here the stray inductance of the transmission is supplemented by another inductance and a capacity to form a resonance circuit. At the same time, the high voltage transmitter is connected directly to the secondary winding of the rotating part. With this arrangement, a certain stray inductance can now be tolerated. However, a very high coupling factor of the rotating data transmission device is needed, because otherwise too large a part of the current would flow through the primary winding of the transmission device as a reactive current. Moreover, with high stray inductance a reasonable matching to the high voltage transmitter would hardly be possible.

A disadvantage of both above-mentioned arrangements is a high outlay of material in the form of costly, highly-permeable ferromagnetic materials. Thus, with typical dimensioning, a few 100 kilograms of iron or ferrite material would be needed. These also would substantially increase the total weight of the computer tomograph. Especially troublesome is the large mass of the rotating part, because this also requires a design of bearing means of suitable strength. Another disadvantage results from the high demands made on mechanical tolerances during rotation between the rotating and the stationary part. Thus, an air gap between the primary side in the stationary part, and the secondary side in the rotating part, should be ideally within a range of a few tenths of a millimeter. However, typical tolerances that can be attained in computer tomographs are larger by almost one order of magnitude. Particularly critical is an operation of a rotating part that is inclined to a horizontal axis, because here the rotating part tilts from its normal position with respect to the stationary part.

BRIEF SUMMARY OF THE INVENTION

The invention is based on the object of designing a device for non-contacting transmission of electrical energy between the stationary and the rotating part of a computer tomograph more economically than in prior art, and furthermore of developing it so that the mass of the entire arrangement is reduced, and also so that larger mechanical tolerances are admissible between the rotating part and the stationary part.

An achievement of this object is set out in the independent patent claims. Further developments of the invention form the subject matter of the dependent claims.

In accordance with the invention, this object is achieved by a computer tomograph system, comprising: a rotating part for accommodating at least one X-ray tube and a detector arrangement; a stationary part for rotatably supporting the rotating part, comprising at least one DC-to-AC converter for generating an alternating current at a first frequency; wherein the stationary part comprises a conductor arrangement mounted to the stationary part by support rods, supplied with alternating current from one or a plurality of the DC-to-AC converters; and wherein the rotating part comprises at least one inductive coupler for engaging, exclusively in dependence upon position, with a section of an entire length of the conductor arrangement, and for coupling electrical energy out of the conductor arrangement.

In accordance with the invention, this object is also achieved by a computer tomograph system, comprising: a rotating part for accommodating at least one X-ray tube and a detector arrangement; a stationary part for rotatably supporting the rotating part, comprising at least one DC-to-AC converter for generating an alternating current at a first frequency; wherein the rotating part comprises a conductor arrangement; and wherein the stationary part comprises at least one inductive coupler supplied with alternating current from one or a plurality of the DC-to-AC converters, for engaging, exclusively in dependence upon position, with a section of the entire length of the conductor arrangement, and for coupling electrical energy into the conductor arrangement.

BRIEF DESCRIPTION OF THE DRAWINGS

In the following the invention will be described by way of example, without limitation of the general inventive concept, on examples of embodiment with reference to the drawings.

DETAILED DESCRIPTION OF PREFERRED EMBODIMENTS

Figure 1:
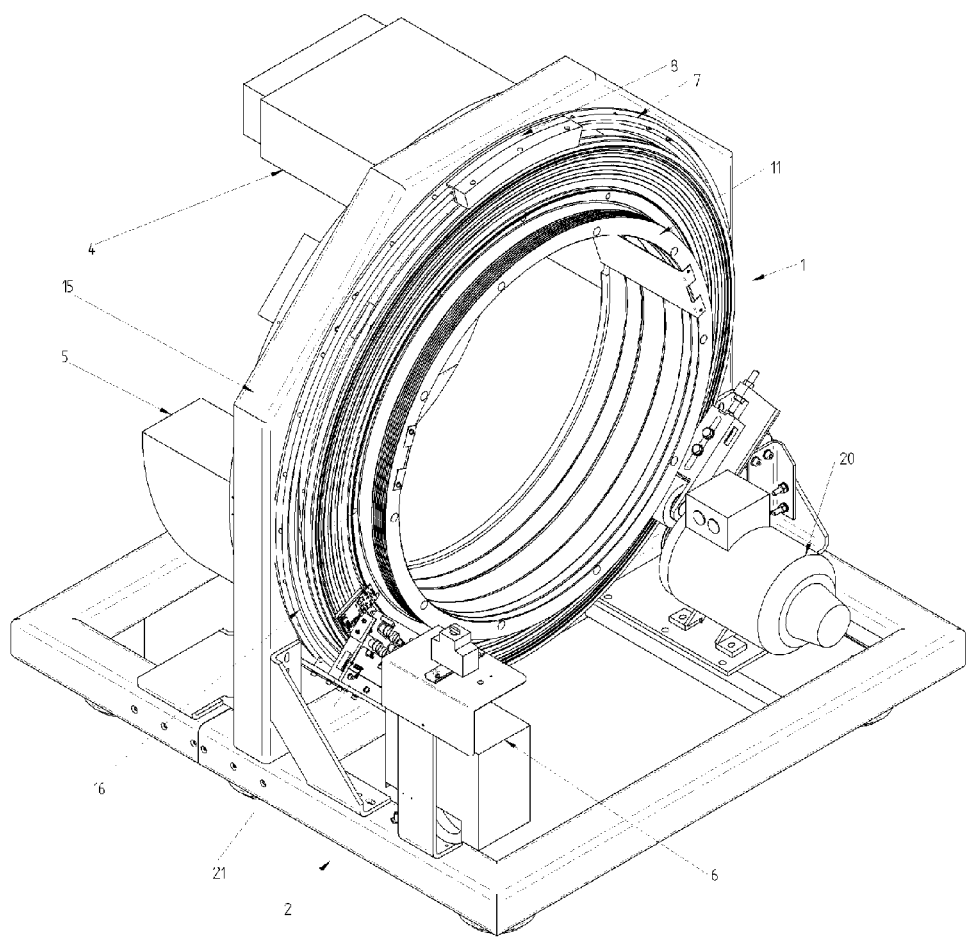
FIG. 1 shows a perspective view of an example of a device in accordance with the invention.

The device in accordance with the invention comprises a computer tomograph with a rotating part 1 and a stationary part 2. The stationary part comprises a bearing assembly for rotatably supporting the rotating part. Furthermore, at least one DC-to-AC converter (inverter) is provided for generating an alternating current. This alternating current contains at least the ground wave of a first frequency. Furthermore, a conductor arrangement is present which is supplied with an alternating current from one or a plurality of DC-to-AC converters. This conductor arrangement is disposed at least along a portion of a circular track on the stationary part. Substantial components of a conductor arrangement in accordance with the invention consist of electrical conductors carried on a mount or on support rods. A conductor arrangement of this kind can be built substantially more easily than the rotating transformers known from prior art which already require, instead of the simple conductor arrangement, a completely designed primary side of a transformer. This comprises, in addition to windings and insulation, also iron or ferrite cores that must be fabricated with small mechanical tolerances to form as small as possible an air gap between the primary side (stationary) and the secondary side (rotating). For coupling out an electric current from the conductor arrangement, an inductive coupler is mounted on the rotating part. This inductive coupler is of a length that is short in comparison with the length of the conductor arrangement, and it is moved by the movement of the rotating part relative to the stationary part along the conductor arrangement. The current coupled out by the inductive coupler can now be supplied to consumers such as the X-ray tube, and also a detector arrangement on the rotating part.

In this description the term "current" is used as a general term to mean electrical energy. Instead of this, reference similarly could be made to the term voltage or energy.

Another device in accordance with the invention is designed similarly to the above-described device. However, the conductor arrangement and the coupler are interchanged. Thus, the coupler is assigned to the stationary part 2 and is supplied with alternating current by the DC-to-AC converter. The conductor arrangement is disposed on the rotating part opposite to the coupler. Accordingly, the current coupled out from the conductor arrangement can now be supplied to consumers such as the X-ray tube, or also the detector arrangement on the rotating part.

A particularly advantageous embodiment of the invention provides a conductor arrangement comprising 1, 2, or even 3 electrical conductors disposed in parallel. Furthermore, currents flow through these conductors so that the sum of the currents through all conductors is equal to zero at each angular position of the conductor arrangement. If, for example, the conductor arrangement is severed by a radial cut at an arbitrary place, and the currents flowing at this place are measured, then the sum of the currents amounts to zero. This may be effected, for example, with a two-conductor system in which a current flows through one conductor in a first direction, and a current of the same magnitude flows through the second conductor in an opposite direction. With a three-conductor system, the currents of the three conductors could each have the same amplitude and be phase-shifted by 120 degrees. With an embodiment of this kind, electromagnetic emission can be substantially reduced. As the sum of the currents at each portion of the conductor arrangement is equal to zero, the outer magnetic field also is zero. In order to achieve good balancing, a balance-unbalance transformer or a common mode filter may be used, for example. For control with a plurality of conductors, a phase-shift-bridge in the DC-to-AC converter is particularly suitable.

In another advantageous embodiment of the invention, the conductor arrangement comprises a plurality of segments along a circumferential direction. With this segmentation, electrical energy of different kinds, such as high power for feeding the X-ray tube, and auxiliary current supplies, may be transmitted via separate segments. Similarly, the entire transmitted power can be increased by connecting a plurality of segments in parallel. Of course, a plurality of conductor arrangements also may be disposed to be parallel to each other, for example adjacently to each other along an axial direction, or inside each other along a radial direction, using suitable couplers.

In another advantageous embodiment of the invention, a plurality of couplers are provided, at least one coupler being in engagement with the conductor arrangement at each instant of time. Here the concept of "instant of time" relates to a rotational movement of the rotating part relative to the stationary part. Expressed differently, this means that at each position of the rotating part, at least one coupler is in engagement with the conductor arrangement. With this, a transmission of energy is possible at each instant of time of the movement, or at each location.

In another advantageous embodiment of the invention, at least one tap comprises magnetically soft material for concentrating the magnetic flux. Thus, the tap may be provided with iron material, preferably in the form of sheet iron, or also ferrite materials, for example. Here a use of iron or ferrite materials, in particular powders bound by plastic material, is of particular advantage. Optionally and additionally, magnetically soft material may be also provided at the conductor arrangement in order to improve mutual coupling.

In another advantageous embodiment of the invention, a plurality of DC-to-AC converters are provided, each DC-to-AC converter energizing optionally one conductor and/or one segment of the conductor arrangement.

In another advantageous embodiment of the invention, at least one DC-to-AC converter is adapted to energize one conductor and/or one segment of the conductor arrangement at, or close to, a respective resonance frequency.

In another advantageous embodiment of the invention, optionally the conductor arrangement, and/or at least one tap, are supplemented with at least one capacitor, and also optionally with one or a plurality of inductances to form a structure capable of resonance at a predetermined resonance frequency. It is especially advantageous for the arrangement to be supplemented to form a series resonance by an addition of a series capacitor, and also an optional series inductance in case the inductances of the conductor arrangement or the tap are not sufficiently large. As an alternative to this, the arrangement can also be designed to form parallel resonances by an addition of at least one parallel capacitor in parallel with the conductor arrangement or the tap. The operation of the DC-to-AC converter may now be adapted to the different resonance conditions. For example, a regulation of the emitted power can be effected by varying the frequency of the DC-to-AC converter. Thus, with an emission of an output current of the DC-to-AC converter at the resonance frequency, a maximum of power is reliably transmitted, whilst smaller power is transmitted at frequency deviations, depending upon the quality of the resonance circuit.

With low load impedances it is of special advantage to regulate the DC-to-AC converter on a series resonance, because this has a quality that increases with sinking load impedance. To the contrary, however, at high load impedances it is of advantage to regulate on a parallel resonance, because with parallel resonances the quality increases with the load impedance. Expediently, a change-over switching means is provided for first determining the load impedance, for example from the ratio of output voltage to output current of the DC-to-AC converter, and then configuring accordingly the frequency regulation of the DC-to-AC converter to parallel resonance or series resonance.

Basically, a system comprising the DC-to-AC converter, the conductor arrangement, and also the tap may be used optionally for transmitting power and simultaneously controlling or regulating the transmitted power, or exclusively for pure power transmission. If the transmitted power is controlled or regulated by the system, then for example, a pulse-width modulation in pulse packages of the output signal, or else a shift of the frequency away from the resonance frequency, is necessary. Basically, the efficiency of the DC-to-AC converter diminishes with a shift of frequency. At the same time, the emissions of high frequency signal components increase. As an alternative to this, the DC-to-AC converter may always be operated at an operating point of optimum efficiency at the resonance frequency. Now, in order to control the emitted output parameter, for example another circuit component, or a power factor correction circuit having an output range settable within wide limits, is needed on the primary side. If the DC-to-AC converter is operated at the resonance frequency, then its efficiency is very high, so that it is not necessary to measure the high-frequency output current in order to measure the transmitted current. Instead, the direct-current consumption of the DC-to-AC converter can be used for this.

In another advantageous embodiment of the invention, at least one DC-to-AC converter is adapted to detect different load conditions, so that it may detect when its assigned segment of the conductor arrangement is not in engagement with at least one tap. In accordance with this detection, the DC-to-AC converter now switches off its output signal or controls it to have a no-load frequency.

Furthermore, at least one DC-to-AC converter can be adapted to emit a signal on at least one second frequency. Moreover, at least one frequency-selective means for selecting this frequency is located on the rotating part, so that it now preferably couples out the energy transmitted with the second frequency and uses this to feed at least one further user such as, for example, a control computer or also the detector arrangement.

In another advantageous embodiment of the invention, the DC-to-AC converter is adapted so that the pulse duty factor of its output current may be varied selectively with a control unit. Advantageously, this does not affect the output frequency. A change of the pulse duty factor changes the spectral distribution of the output current. Thus, with a pulse duty factor of 50%, corresponding to that of a symmetrical output signal, the proportion of even-number multiples of the base frequency f0, i.e. $2 \cdot f0$, $4 \cdot f0$, $6 \cdot f0$ etc. approaches zero in an ideal case. If the pulse duty factor is changed to that of non-symmetrical output currents, for example only slightly to 49 and 48 percent, or on a large scale to 40 or 30 percent, then the amplitude of the even-number multiples increases. By selective filtering of the even-number multiples on the rotating part, a predetermined proportion of the transmitted power may be coupled out, for example to supply small consumers such as a control computer or the detector arrangement. In an advantageous manner, an auxiliary supply means may be provided to undertake a supplying to small loads in case the DC-to-AC converter configured for issuing high power is not active, because for example, no supply need be made to the X-ray tube.

Another advantageous embodiment of the invention provides at least one DC-to-AC converter for issuing a frequency-modulated output current. A modulation of the output frequency leads to a broadening of individual spectral lines of an output signal, whilst the signal amplitude is simultaneously reduced. This results in improved EMC properties of the system. The modulation frequency should be selected to be greater than or equal to 100 Hz, so that it is larger than a measurement interval of the usual EMC Standards. Furthermore, the modulation amplitude, i.e. the frequency variation, should be chosen to be only so small that no appreciable fluctuations of the current result on the rotating side.

Figure 2:
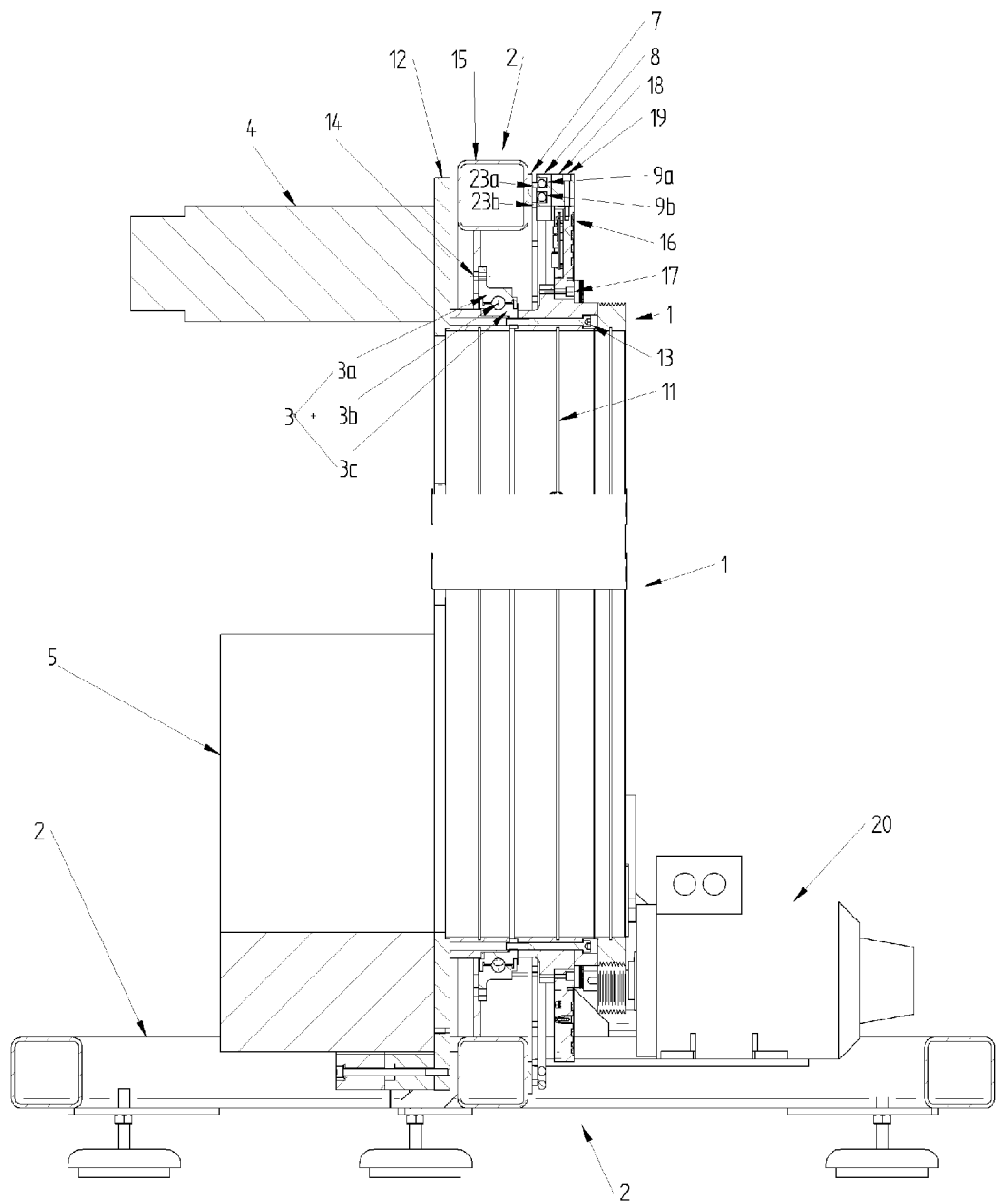
FIG. 2 shows in a schematic form a sectional view of a device in accordance with the invention as depicted in FIG. 1.

FIG. 1 shows a perspective view of an example of a device in accordance with the invention. FIG. 2 shows in a schematic form a sectional view of the device shown in FIG. 1. In this, the components depicted in FIG. 1 are denoted by the same reference symbols. The device shown in FIGS. 1 and 2 is a computer tomograph (CT scanner) consisting essentially of two main mechanical components. A stationary part 2 serves as a base and frame of the entire instrument in which a rotating part revolves. A patient is positioned on a berth within an opening of the rotating part. A bearing assembly 3 retained by a hollow section 15 of the stationary part 2 serves to support the rotating part 1. In the example of embodiment, this bearing assembly is designed to be a ball bearing. Of course, various other types of bearing may be used for this. An X-ray tube 4 and an oppositely disposed detector 5 are provided for scanning the patient by means of X-rays. The X-ray tube 4 and the detector 5 are disposed to be rotatable on the rotating part 1. A motor 20 is provided to drive the rotating part. A slip ring 16 mounted on the rotating part 1 serves, together with a slip-ring tap 21 attached to the stationary part, for a transmission of auxiliary and control signals. Thus, for example, safety signals such as those enabling X-radiation may still be transmitted via mechanical sliding contacts, as is at present still required by safety standards. As an alternative to this, an activation signal for the X-ray tube could also be transmitted without contact. In order to satisfy safety standards, this signal would have to be repeated at regular time intervals. If the signal is no longer received by the rotating part at these time intervals, then the X-ray tube is deactivated. The two sliding contacts that are still necessary in a mechanical configuration are almost free from requiring maintenance because of the low current load, and cause substantially less abrasion, and thus less contamination, than the contacts previously employed for transmission of energy. With this arrangement, image data of the detector arrangement 5 can be transmitted in parallel with this to the stationary part 2, for example without contact. For energy transmission, i.e. in particular for transmitting the high energy that is required by the X-ray tube, a conductor arrangement 7 powered by a DC-to-AC converter (inverter) 6 is provided on the stationary part 2. A tapping of signals from this conductor arrangement 7 is effected by means of a coupler 8 on the rotating part 1. At least one coupler 8 should be provided to safeguard the operation. Of course, a plurality of couplers 8 may be provided. Optionally these may be connected in parallel, but also adapted for individually tapping-off supply energy for the X-ray tube 4, the detector arrangement 5, or other electronic components.

Figure 3:
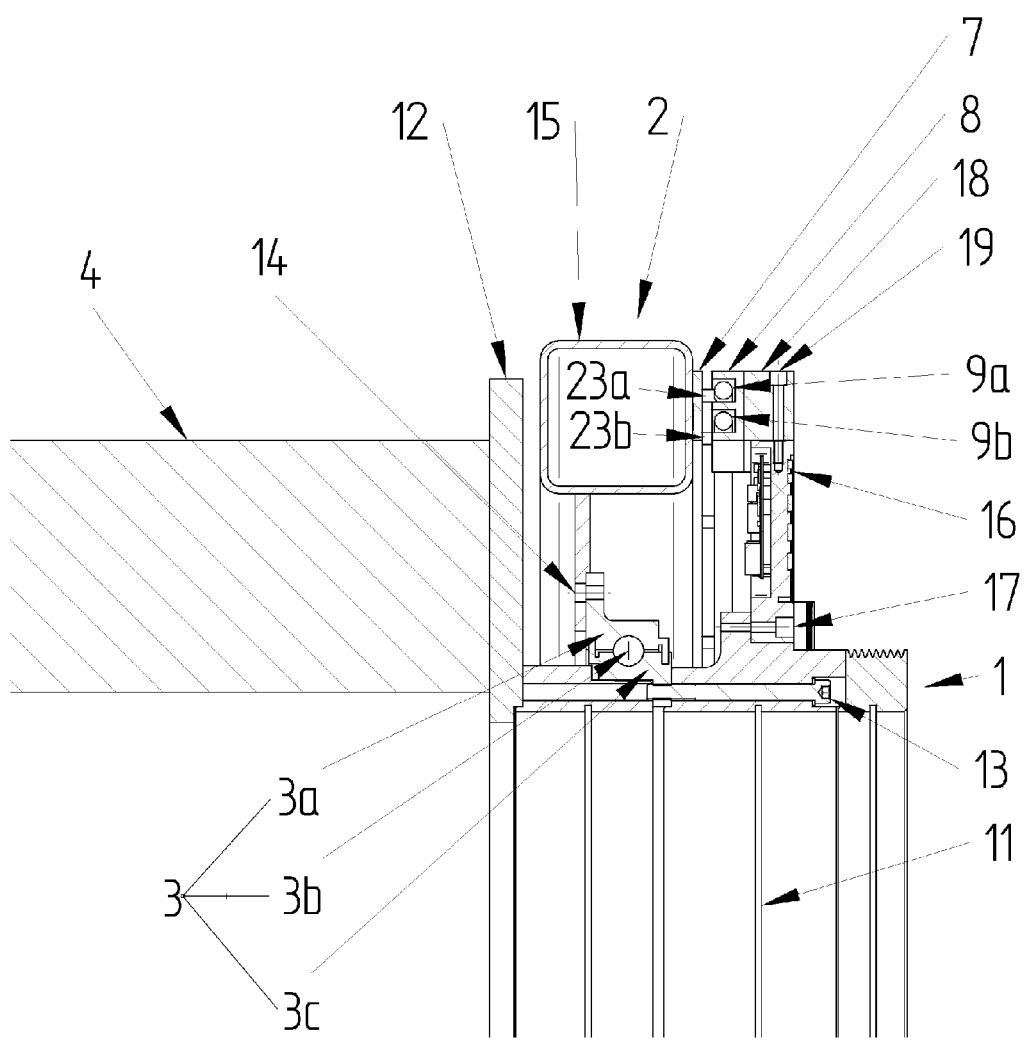
FIG. 3 shows a cutout portion of an upper region of FIG. 2 of a device in accordance with the invention.

FIG. 3 shows a cutout portion of an upper region of FIG. 2 of a device in accordance with the invention. Most of the previously described components can be recognized more clearly in this illustration. Furthermore, an operative relationship between the parts becomes more clearly evident. In the illustrated region the stationary part 2 is designed to be a hollow section in order to increase the stability. The rotating part 1 is rotatably supported on this by means of a bearing assembly 3. The roller-bearing assembly 3 comprises an outer fixed (stationary) bearing ring 3a that is secured by means of a plurality of screws 14 to the stationary part 1. Confronting this, an inner bearing ring 3c is rotatably supported by means of balls 3b. Fastened to one side of this by means of a plurality of fastening bolts 13 (shown in section on the right-hand side) is a cylinder 11, and to the other side a disk 12. The disk 12 carries most of the components mounted to the rotating part 1, such as the X-ray tube 4 and the detector arrangement 5, in particular. The cylinder 11 carries a slip ring 16 secured to the cylinder 11 by means of screws 17. Mounted to this slipring, here by way of example, is a coupler 8 on a supporting member 18 that is fastened to the slipring 16 by means of screws 19. Here, for example, this coupler 8 has a U-shaped core of a magnetically soft material, such as, for example, iron or ferrite material. For transmission of energy, the coupler 8 is engaged with the conductor arrangement 7. The conductor arrangement 7 depicted here has two parallel conductors 9a and 9b, for example. These conductors are mounted to the stationary part 2 by means of support rods 23a and 23b. As set forth below, a support plate 41 consisting preferably of a magnetically soft material 44 is provided for exact positioning and easy assembly of the conductor arrangement 7 (see, e.g., FIGS. 5-8).

Figure 4:
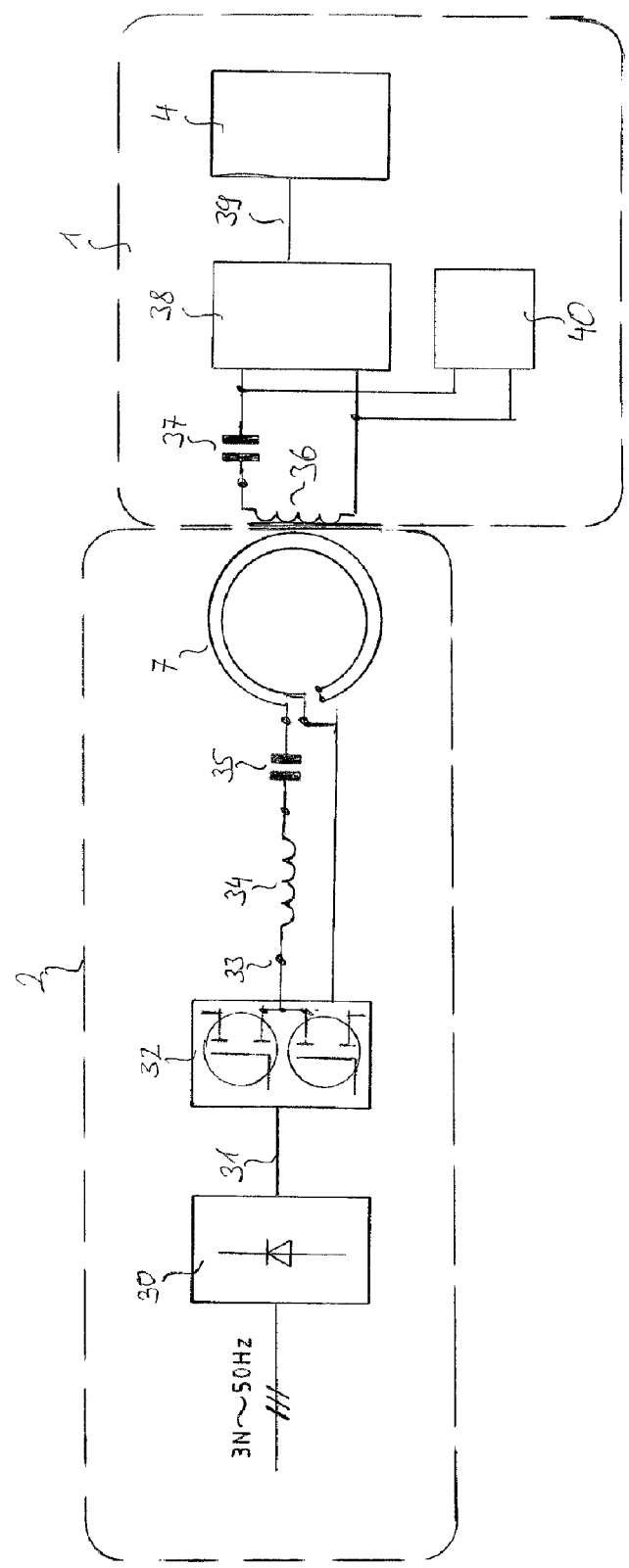
FIG. 4 shows a block diagram of an electrical circuit of an example of a device in accordance with the invention.

FIG. 4 depicts a block diagram of an electrical circuit of an example of a device in accordance with the invention. Current supply to the entire arrangement is effected preferably via a three-phase line supply having a conventional line frequency which in the present case is 50 Hz, for example. Of course, a two-phase or d.c. supply is also possible. Input circuitry 30 comprises usual filters and a rectifier circuit, preferably with power factor correction (PFC). Rectified current at an output 31 is converted to a high-frequency alternating current by means of a DC-to-AC converter (inverter) 32 having typically 2, 4, or more semiconductor power switches. These semiconductor power switches may be configured, for example, as known half-bridge or full-bridge circuits. Preferably suitable as semiconductor switches are IGBTs or MOSFETS. The preferred frequency range is higher than that of the human threshold of audibility, i.e. 20 kHz, and extends as far as an upper frequency of about 1 MHz up to which modern high-power semiconductor-switches can be used economically. The high-frequency alternating current is issued from an output 33 and fed into the conductor arrangement 7 by means of a series inductance 34 and a series capacitance 35.

The resonance frequency of the arrangement results from the inductance 34 and also the inductance of the conductor arrangement 7 together with the capacitance 35. If the inductance of the conductor arrangement is sufficiently high, then the inductance 34 may be dispensed with. The inductance of the conductor arrangement 7 is composed of an inductance of the conductor itself, a transformed inductance 36 of the coupler 8, and also a coupling factor between the conductor arrangement 7 and the coupler 8. The output current tapped off from the coupler 8 can now be passed to a high voltage generator 38 producing a high voltage 39 for energizing the X-ray tube 4. A number of other consumers 40 also may be supplied in parallel with the high voltage generator 38. A connection to the coupler 8 may be effected optionally directly or by interposing a series capacitance 37. This results in a second resonance circuit 36, 37 on the secondary side. Operation of the inverter is effected expediently on or close to the resonance frequency of the system. Control of transmitted power may be performed, for example, by controlling the operating frequency of the inverter, so that at low power requirement, a frequency remote from the resonance frequency is chosen. Similarly, however, control of power may be effected by input circuitry 30 that sets its DC voltage according to the power requirement. In this case, the inverter connected to follow may be operated at maximum efficiency on the resonance frequency of the circuit.

In order to match the impedance conditions it may be necessary to insert transformers at various sites of the arrangement. This may be necessary particularly between the DC-to-AC converter 6 and the conductor arrangement 7, and also between the coupler 8 and the load. If the DC-to-AC converter is used to feed the coupler 8, then a transformer should be provided between the DC-to-AC converter and the coupler, or between the coupler arrangement and the load. It is equally expedient to insert a balancing transformer (having a high quality core of magnetically soft material), or a common mode choke having a magnetically soft core attended by losses, particularly to follow the DC-to-AC converter, or on the conductor arrangement.

In addition, a regulating means for the supplied voltage or the supplied current may be provided on the load side, for example by means of a switching power supply. Thus, the high voltage generator 38 and also an auxiliary supply means 40 will certainly be provided with regulating means for the output voltage.

Figure 5:
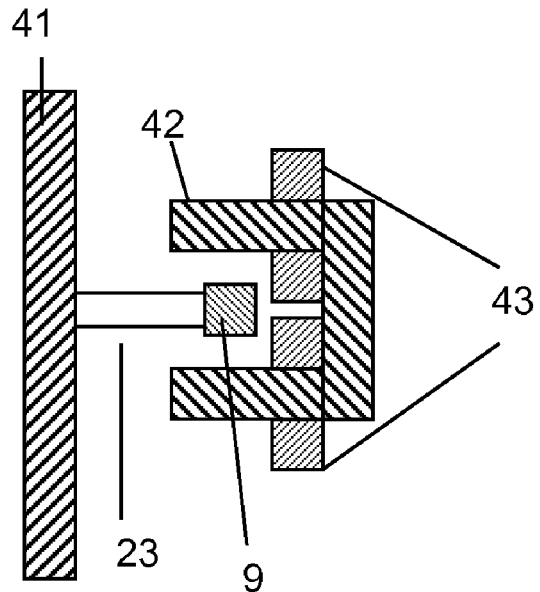
FIG. 5 depicts an arrangement with one single conductor.

FIG. 5 illustrates an arrangement with one single conductor. A bearer means 41 for the entire conductor arrangement, that may consist of, for example, metal for screening, but also an insulating material, carries an electrical conductor 9 by means of a support rod 23. For tapping-off current, a coupler comprising a core 42 of a magnetically soft material, and a winding 43 for coupling out an electric current, run along the conductor.

Figure 6:
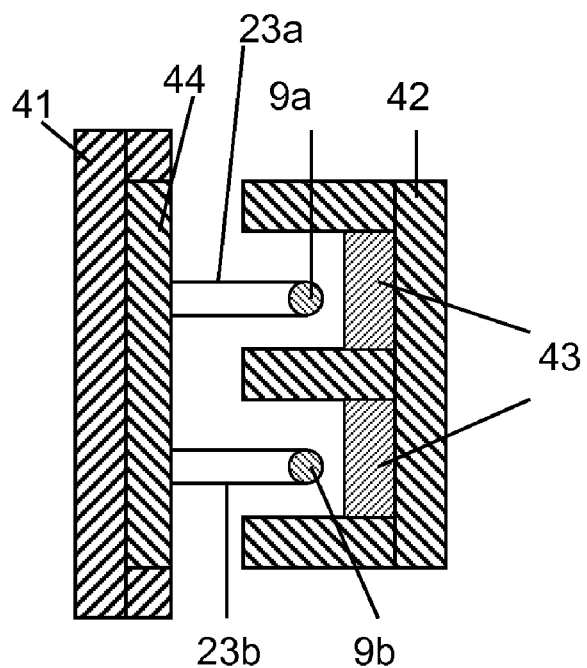
FIG. 6 shows an arrangement with two electrical conductors.

FIG. 6 shows an arrangement with two electrical conductors. Here the conductor arrangement comprises a bearer means 41 and, disposed thereon, a magnetically soft material 44 for conducting a magnetic field. Parallel electrical conductors 9a and 9b are supported by means of support rods 23a and 23b. Here the coupler comprises a U shaped core 42 of a magnetically soft material, having at least one winding 43.

Figure 7:
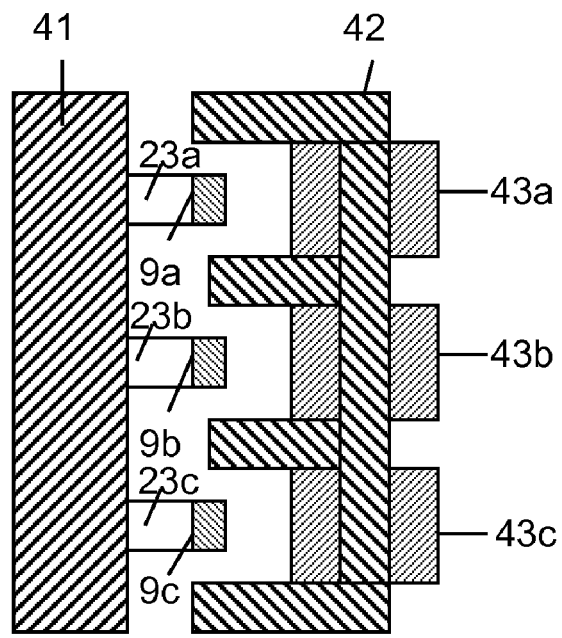
FIG. 7 shows an arrangement with three electrical conductors.

FIG. 7 illustrates a corresponding arrangement with three conductors. Conductors 9a, 9b, 9c are attached to the bearer means with support rods 23a, 23b, 23c. Here the coupler is provided with three windings 43a, 43b, 43c.

Figure 8:
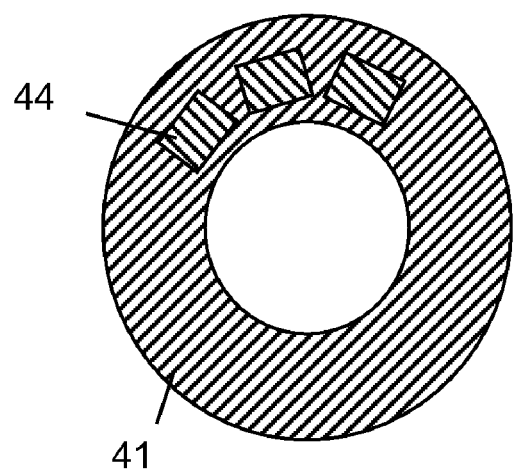
FIG. 8 shows a bearer 41 with plates of a magnetically soft material 44 mounted thereon.

FIG. 8 shows a bearer means 41 with plates of a magnetically soft material 44 mounted thereon. With an arrangement of this kind, a simple encasing of the bearer means can be effected with prefabricated plate sections that are optionally rectangular or fitted to rounded portions. It is expedient for not only a portion of the circular circumference, as shown in the drawing for the sake of simplicity, but the entire circular circumference to be encased with plate sections.

Figure 9:
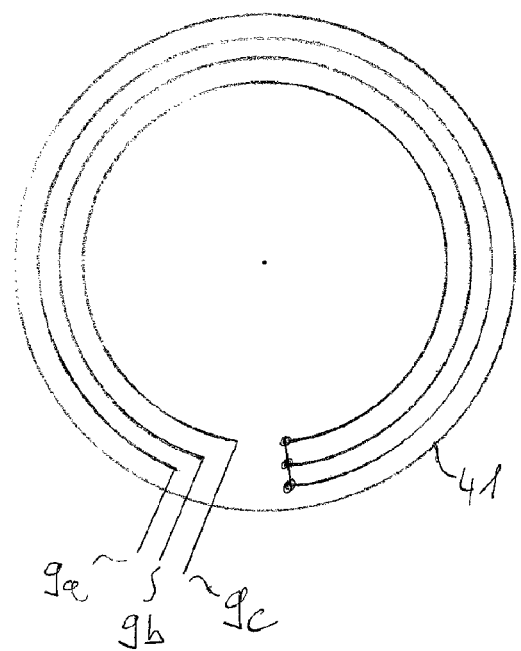
FIG. 9 shows an arrangement with three conductors disposed in parallel.

FIG. 9 illustrates an embodiment of the invention with three conductors disposed in parallel. These are arranged on the bearer means 41. The open ends are supplied with current from DC-to-AC converters. Here by way of example, the three conductors are connected together at one end. Expediently, each of the currents supplied by the DC-to-AC converter is phase-shifted by 120 degrees with respect to the others. Of course, in addition to the arrangement with three conductors shown here, any other number of conductors may be used.

Figure 10:
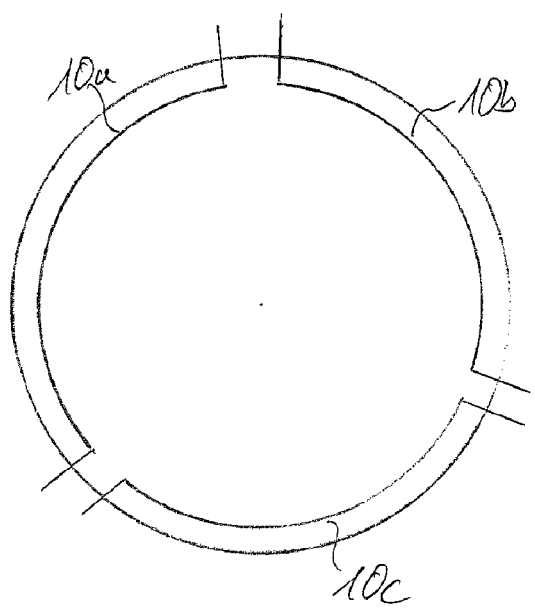
FIG. 10 shows an arrangement with segmented conductors.

FIG. 10 shows an embodiment of the invention in which the conductors are divided into conductor segments 10a, 10b, 10c. Three conductors are shown by way of example, but similarly two or more conductor segments may be employed. Each one of the conductor segments by itself may consist of one or a plurality of conductors disposed in parallel. Current supply is effected with a common DC-to-AC converter, or with an individual DC-to-AC converter for single conductor segments or groups of conductor segments. In addition to a frequency division multiplex, here also a local multiplex may be used for transmission. For this, it is expedient to employ a plurality of couplers 8. With this, a plurality of supply currents, for example for the X-ray tube, and also for the detector arrangement or other consumers, may be transmitted separately from each other.

The invention claimed is:

1. A computer tomograph system, comprising:
   a rotating part for accommodating an X-ray tube and a detector;
   a stationary part for rotatably supporting the rotating part, comprising at least one DC-to-AC converter for generating an alternating current at a first frequency;
   a conductor mounted to the stationary part by support rods and supplied with alternating current from one or a plurality of the DC-to-AC converters, wherein the conductor extends as a straight line in a rotating first plane, and an arcuate line in another plane perpendicular to the first plane along a rotational path in which the rotating part rotates; and
   an inductive coupler mounted to the rotating part for movement along the straight, arcuate line of the conductor for coupling electrical energy out of the conductor as the rotating part rotates.

2. The computer tomograph system according to claim 1, wherein the conductor further comprises 2 or 3 parallel conductors through which electric currents flow so that the sum of the currents through all conductors is zero at every place of the conductor arrangement.

3. The computer tomograph system according to claim 1, wherein the conductor comprises a plurality of segments along a circumferential direction.

4. The computer tomograph system according to claim 3, wherein a plurality of DC-to-AC converters are provided, each supplying current to one segment of the conductor.

5. The computer tomograph system according to claim 4, wherein at least one DC-to-AC converter is adapted to supply current to one segment of the conductor at or close to a respective resonance frequency.

6. The computer tomograph system according to claim 1, wherein a plurality of couplers are provided, at least one coupler being engaged with the conductor at any instant of time.

7. The computer tomograph system according to claim 6, wherein at least one coupler comprises magnetically soft material for concentrating magnetic flux.

8. The computer tomograph system according to claim 1, wherein at least one series capacitance is connected in series with the conductor or the coupler.

9. The computer tomograph system according to claim 1, wherein at least one parallel capacitance is connected in parallel with the conductor or the coupler.

10. The computer tomograph system according to claim 1, wherein at least one DC-to-AC converter is adapted to detect a condition in which the conductor, or a segment of the conductor, is not engaged with at least one coupler, and to be switched off or controlled to a no-load frequency in case of non-engagement.

11. The computer tomograph system according to claim 1, wherein at least one DC-to-AC converter is adapted to issue an alternating current of at least one second frequency to supply current to at least one other consumer, and wherein at least one coupler, or a circuitry of a coupler, is adapted to be frequency selective to select the at least one second frequency, and to pass substantially a tapped-off signal or tapped-off energy having the second frequency to at least one other consumer.

12. The computer tomograph system according to claim 1, wherein at least one DC-to-AC converter is adapted to issue an alternating current at a variable pulse-width repetition rate, and wherein a filter unit is provided on the rotating part to select frequency components with whole-number multiples of the first frequency, and to supply current having the selected frequency components to at least one other consumer.

13. The computer tomograph system according to claim 1, wherein at least one DC-to-AC converter is adapted to issue an alternating current having a modulated output frequency, a frequency sweep being chosen to be so small that no significant fluctuations of amplitude of an output current occur, and simultaneously the modulation frequency being chosen to be higher than, or equal to, 100 Hz.

14. A computer tomograph system, comprising:
    a rotating part for accommodating an X-ray tube and a detector;
    a stationary part for rotatably supporting the rotating part, comprising at least one DC-to-AC converter for generating an alternating current at a first frequency;
    a conductor mounted to the rotating part; and
    an inductive coupler mounted to the stationary part and partially surrounding the conductor, along the length of the conductor, as the conductor moves correspondingly with rotation of the rotary part, wherein the coupler is supplied with alternating current from one or a plurality of the DC-to-AC converters for coupling electrical energy into the conductor.

15. The computer tomograph system according to claim 14, wherein the conductor further comprises 2, or 3 parallel conductors through which electric currents flow so that the sum of the currents through all conductors is zero at every place of the conductor arrangement.

16. The computer tomograph system according to claim 14, wherein the conductor comprises a plurality of segments along a circumferential direction.

17. The computer tomograph system according to claim 14, wherein a plurality of couplers are provided, at least one coupler being engaged with the conductor at any instant of time.

18. The computer tomograph system according to claim 14, wherein at least one coupler comprises magnetically soft material for concentrating magnetic flux.

19. The computer tomograph system according to claim 14, wherein a plurality of DC-to-AC converters are provided, each supplying current to one segment of the conductor.

20. The computer tomograph system according to claim 14, wherein at least one DC-to-AC converter is adapted to supply current to one segment of the conductor at or close to a respective resonance frequency.

21. The computer tomograph system according to claim 14, wherein at least one series capacitance is connected in series with the conductor or the coupler.

22. The computer tomograph system according to claim 14, wherein at least one parallel capacitance is connected in parallel with the conductor arrangement or the coupler.

23. The computer tomograph system according to claim 14, wherein at least one DC-to-AC converter is adapted to detect a condition in which the conductor, or a segment of the conductor, is not engaged with at least one coupler, and to be switched off or controlled to a no-load frequency in case of non-engagement.

24. The computer tomograph system according to claim 14, wherein at least one DC-to-AC converter is adapted to issue an alternating current of at least one second frequency to supply current to at least one other consumer, and wherein at least one coupler, or a circuitry of a coupler, is adapted to be frequency selective to select the at least one second frequency, and to pass substantially a tapped-off signal or tapped-off energy having the second frequency to at least one other consumer.

25. The computer tomograph system according to claim 14, wherein at least one DC-to-AC converter is adapted to issue an alternating current at a variable pulse-width repetition rate, and wherein a filter unit is provided on the rotating part to select frequency components with whole-number multiples of the first frequency, and to supply current having the selected frequency components to at least one other consumer.

26. The computer tomograph system according to claim 14, wherein at least one DC-to-AC converter is adapted to issue an alternating current having a modulated output frequency, a frequency sweep being chosen to be so small that no significant fluctuations of amplitude of an output current occur, and simultaneously the modulation frequency being chosen to be higher than, or equal to, 100 Hz.

* * * * *